(12) United States Patent
Vidal (10) Patent No.: US 10,207,061 B2
(45) Date of Patent: Feb. 19, 2019

(54) MULTI-CHAMBERED DISPENSER FOR THE TOPICAL APPLICATION OF INFUSED FLUID

(71) Applicant: Michelle Vidal, Valencia, CA (US)

(72) Inventor: Michelle Vidal, Valencia, CA (US)

( * ) Notice: Subject to any disclaimer, the term of this patent is extended or adjusted under 35 U.S.C. 154(b) by 37 days.

(21) Appl. No.: 15/247,657

(22) Filed: Aug. 25, 2016

(65) Prior Publication Data

US 2018/0056012 A1   Mar. 1, 2018

(51) Int. Cl.
| | | |
|---|---|---|
| A61M 11/00 | (2006.01) | |
| A61M 35/00 | (2006.01) | |
| A61K 31/375 | (2006.01) | |
| A61K 33/12 | (2006.01) | |
| A61K 33/26 | (2006.01) | |
| A61K 33/06 | (2006.01) | |
| A61K 33/24 | (2006.01) | |
| A61K 9/00 | (2006.01) | |

(52) U.S. Cl.
CPC ......... *A61M 11/006* (2014.02); *A61K 31/375* (2013.01); *A61K 33/06* (2013.01); *A61K 33/12* (2013.01); *A61K 33/24* (2013.01); *A61K 33/26* (2013.01); *A61M 35/003* (2013.01); *A61K 9/0014* (2013.01)

(58) Field of Classification Search
CPC .. A61M 5/003; A61M 11/006; A61M 35/003; A61K 9/08; A61K 9/0014; A61K 31/375; A61K 33/06; A61K 33/12; A61K 33/24; A61K 33/26

USPC ... 222/190, 382, 383.1, 189.06–189.11, 333, 222/464.2, 464.7
See application file for complete search history.

(56) References Cited

U.S. PATENT DOCUMENTS

| | | | | |
|---|---|---|---|---|
| 1,019,171 A | * | 3/1912 | Melville-Hamilton | ...................... B05B 11/0059 210/245 |
| 4,634,028 A | * | 1/1987 | de Larosiere | .......... B65D 25/02 215/10 |
| 5,059,805 A | * | 10/1991 | Shimizu | ................... G21H 5/00 250/436 |
| 5,306,511 A | * | 4/1994 | Whang | .................. A61K 33/00 426/66 |
| 6,013,180 A | * | 1/2000 | Wang | ..................... C02F 1/003 210/232 |

(Continued)

*Primary Examiner* — Paul R Durand
*Assistant Examiner* — Andrew P Bainbridge
(74) *Attorney, Agent, or Firm* — Risso I.P.

(57) ABSTRACT

A multi-chambered dispenser which both retains solid objects such as mineral and ceramic stones in a defined region and also enables fluid communication with the objects is provided. A permeable inner wall may be disposed within an outer chamber to define a barrier preventing the solid objects maintained within the outer chamber from entering an inner chamber defined by the permeable inner wall. Fluid, such as tap or even filtered water, may be poured into the dispenser, and, owing to the permeation of the inner wall, freely communicate with the objects maintained outside of the permeable inner wall to absorb and become infused with various beneficial characteristics comprising the objects. Means for dispensing the infused fluid for topical application may be configured to draw infused fluid out of the dispenser through the inner chamber such that interference of such means by the solid objects is avoided.

20 Claims, 4 Drawing Sheets

(56) References Cited

U.S. PATENT DOCUMENTS

| | | | | |
|---|---|---|---|---|
| 6,136,189 A * | 10/2000 | Smith | ................... | C02F 1/002 210/266 |
| 6,250,508 B1 * | 6/2001 | Geser | ................... | B05B 9/03 222/189.1 |
| 6,569,329 B1 * | 5/2003 | Nohren, Jr. | ................... | B01D 29/15 210/282 |
| 6,919,025 B2 * | 7/2005 | Cluff | ................... | C02F 1/002 210/244 |
| 7,427,355 B2 * | 9/2008 | Chau | ................... | C02F 1/002 210/223 |
| 8,091,741 B2 * | 1/2012 | Pritchard | ................... | B05B 11/0043 222/189.1 |
| 8,657,162 B2 * | 2/2014 | Kelly | ................... | B01F 13/002 222/158 |
| 8,741,137 B2 * | 6/2014 | Ruprecht | ................... | B01D 35/30 210/232 |
| 9,469,550 B2 * | 10/2016 | Closi, Jr. | ................... | C02F 1/002 |
| 9,636,696 B2 * | 5/2017 | Hextall | ................... | B05B 11/0086 |
| 9,663,691 B2 * | 5/2017 | Adams | ................... | A23F 5/00 |
| 2005/0252844 A1 * | 11/2005 | Chau | ................... | C02F 1/002 210/282 |
| 2006/0032753 A1 * | 2/2006 | Hsien | ................... | C02F 1/4618 204/660 |
| 2006/0231502 A1 * | 10/2006 | Ito | ................... | C02F 1/461 204/278.5 |
| 2007/0181605 A1 * | 8/2007 | Yang | ................... | B05B 15/30 222/321.5 |
| 2008/0006718 A1 * | 1/2008 | Junkel | ................... | A45F 3/16 239/333 |
| 2009/0065732 A1 * | 3/2009 | Yeh | ................... | A01N 59/00 252/62.9 R |
| 2009/0173673 A1 * | 7/2009 | Pritchard | ................... | B01D 63/025 210/85 |
| 2010/0301132 A1 * | 12/2010 | Wagstaff-Bellomo | ................... | A61L 9/042 239/36 |
| 2012/0091070 A1 * | 4/2012 | Sjauta | ................... | C02F 1/003 210/764 |
| 2012/0267400 A1 * | 10/2012 | Mohr | ................... | B05B 11/001 222/331 |
| 2014/0008395 A1 * | 1/2014 | Syed | ................... | B05B 11/3042 222/321.5 |
| 2014/0343487 A1 * | 11/2014 | Hlebnikov | ................... | A61J 7/0038 604/77 |
| 2016/0244648 A1 * | 8/2016 | Adams | ................... | A23F 5/00 |
| 2018/0056012 A1 * | 3/2018 | Vidal | ................... | A61M 11/006 |

\* cited by examiner

FIG. 4

MULTI-CHAMBERED DISPENSER FOR THE TOPICAL APPLICATION OF INFUSED FLUID

GOVERNMENT CONTRACT

Not applicable.

CROSS-REFERENCE TO RELATED APPLICATIONS

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to dispensers and, more particularly, to an apparatus defined by multiple chambers configured to retain solid objects in a defined region but also permit fluid communication with the solid objects and is further operative to dispense fluid combined with traces of the solid objects for topical application.

BACKGROUND

Enhanced or ionized topical formulations are frequently associated with a variety of health benefits and have recently gained popularity for that reason. By way of example, water enhanced by alkaline materials contains antioxidants which are thought to combat free radicals within a person's body and increase the pH of a user's body. As a result, it is believed that alkali-enhanced water may boost a user's immune system and slow his or her aging process.

It has been suggested that using enhanced formulations may beneficially increase a user's bodily alkalinity levels, which can become more acidic as a result of eating fatty and processed foods. In some cases, an abundance of acid in one's body can lead to stomach pains, headaches, and fatigue. Additionally, some enhanced molecules, such as alkaline water molecules, form smaller clusters than do non-enhanced water molecules. It is thought that these smaller, enhanced water molecule clusters are more readily absorbed—as compared to the larger molecule clusters—by cells within the body which may cause the user to feel more hydrated than if he or she had used non-enhanced water.

It has also been proposed that using formulations enhanced by alkaline materials can decrease the risk of osteoporosis by decreasing the body's acidity. This is because an overly-acidic bodily environment can cause calcium loss, which may result in damaged and degraded bones.

As another example, bacteria known to develop on skin and in pores tend to thrive in acidic environments. Alkali-enhanced formulations may thus be externally or topically applied to a user's skin to reduce the acidity and habitability for bacteria of the skin and decrease amount of bacteria and dwelling within the user's pores, which in turn, may enhance the cleanliness and overall health of a user's skin.

One way that consumers have obtained enhanced formulations is to buy pre-packaged beverage bottles containing enhanced water and other fluid formulations. However, providing enhanced fluids in this manner fails to conveniently enable topical application the enhanced formulations.

A second method of obtaining enhanced formulations is for a user to take an un-enhanced formulation and personally add an enhancing solution so that the formulation becomes enhanced. For example, U.S. Pat. No. 5,306,511 issued to Whang discloses an alkali booster solution that a user may add to his or her regular bottled water or tap water. The proposal is deficient, however, because it suggests adding booster solution to water each time boosted water is desired. In other words, it requires the user to always have the alkali booster solution on hand which can be tedious and cumbersome and prone to inconvenience due to forgetfulness.

Yet another method of obtaining enhanced formulations is to attach an alkali filter to a water faucet. By way of example, U.S. Pub. No. 2006/0032753 filed by Hsien teaches a faucet that contains a water filter and an electrolyzing machine that adds elements to the filtered water which results in enhanced water. This system is deficient, however, because alkali filters are generally limited for use in combination with a particular faucet. They are not easily transferred between remote faucets, making them non-ideal for those seeking readily available topically applicable enhanced water.

Although various proposals have been made to solve the problem, none of those in existence combine the characteristics of the present invention. Therefore, there is a need for a portable device that allows a user to topically enjoy potential benefits of enhanced water.

SUMMARY

The present disclosure is directed to a dispenser for various topical formulations such as tap and/or filtered water and other fluids enhanced or infused with desirable minerals. More particularly, the device may comprise multiple chambers configured to contain, for example, a fluid and an at least one fluid-enhancing solid object, such as a mineral stone. In practice, the fluid may mix with the at least one fluid-enhancing solid object and absorb trace minerals comprising the object to create an enhanced solution that a user to may apply to his or her skin via the dispenser.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

In accordance with one embodiment, the dispenser may comprise an impermeable outer chamber defined by a top wall, a bottom wall, and at least one side wall. The top wall may further define an opening through which any contents within the dispenser may be dispensed. The impermeable walls may be comprised of a durable material. For example, it is contemplated that acrylic plastic may comprise the top, bottom, and side walls. However, other types of materials, such as tempered glass, acetal resin, metal, high-density polyethylene, and other materials known to those skilled in the art are also contemplated.

Next, at least one permeable wall may be enclosed within the outer chamber to define a permeable inner chamber. The permeable wall may be affixed within the impermeable outer chamber to the impermeable bottom wall and extend upward to the impermeable top wall to define a space between an outside of the permeable wall and an inside of the walls comprising the outer chamber, within which an at least one solid object may be maintained. In one embodiment, the permeable inner chamber may be at least as wide as the opening defined by the impermeable top wall so that the permeable inner wall may define a superposed extension of the opening defined by the impermeable top wall of outer chamber.

In one embodiment, the permeable inner wall may define a plurality of openings that permit fluid communication between the inner and outer chambers. Still, it is contemplated that said openings may be smaller than the at least one solid object contained within the space between the permeable wall and the impermeable walls so that said at least one solid object retained therein may be prevented from entering the inner chamber while avoiding the disruption of fluid communication between the chambers. Of course it is contemplated that various materials are available to form the permeable wall. One skilled in the art will, for example and not limitation, recognize that the permeable inner wall may comprise durable mesh, PVC, metal and others able to maintain their structure in wet and mineral-rich environments.

It may be desirable that the inner chamber remain free of the at least one solid object because the at least one solid object may create a blockage or other disruption preventing any fluid within the dispenser from being dispensed. Thus, ensuring that any holes or mesh defined by the permeable inner wall are smaller than the solid objects and further superposing the inner chamber with the opening in the top wall may ensure that the at least one solid object is prevented from entering the inner chamber through any portion of the permeable inner wall.

The dispenser may be filled with a topical formulation such any fluid known in the art to be suitable for application on skin. The fluid may comprise non-enhanced water, such as tap or filtered water. However, other physically fluid substances, such as foam, lotion, and even gel may be used for the formulation. Any substance that is able to fluidly communicate between the inner chamber and the outer chamber through the inner wall is contemplated by the invention.

The at least one solid object retained in the space defined by the outside of the permeable inner wall and the inside of the impermeable outer walls may comprise, for example only and not limitation, one or more mineral stones which are known to impart traces of their composite ingredients that may be absorbed by water and other fluids that come into contact with them. Providing such objects in solid form may ensure that minerals and other beneficial ingredients may be released, absorbed by, or otherwise mixed with fluid contained by the dispenser over a prolonged period of time. This may prolong the utility of the dispenser, though it is contemplated that mineral stones and other infusing and/or enhancing objects retained in the space between the inside of the outer chamber and outside of the inner chamber may be replaced when, for example and not limitation, their beneficial characteristics have been depleted.

In an embodiment, such mineral stones may cause the pH of the fluid contained within the dispenser to rise. Such mineral stones may comprise one or a combination of tourmaline, sepiolite, negative ion powder, ascorbic acid, germanium, magnesium, calcium, ceramic minerals, and muyu jade stone. More particularly, tourmaline may be beneficial, for example, because it generates negative ions which can electrolyze the fluid. Germanium may be useful in boosting a user's immune system and destroying undesirable free radicals. Muyu jade stones have been reported to slow the aging process in humans. The use of a plurality of mineral stones as the solid object composed of at least one of these substances, among others, may be beneficial because the substances may possess alkaline characteristics and properties that may be easily absorbed over time by fluid contained within the dispenser and communicating with the stones. Of course it is contemplated that other minerals, compounds, and substances known to those skilled in the art may be used to enhance the formulation, such as clay and sodium bicarbonate, thus the foregoing are offered by way of example only and not of limitation.

In an embodiment, the opening defined by the top wall of the dispenser may be configured to securely receive a means for dispensing the liquid or other topical formulation contained within the dispenser. In one embodiment, the means for dispensing may comprise a pump, such as but not limited to a mist sprayer pump configured to disperse discrete droplets. Since a mist sprayer pump may dispense the formulation in fine droplets, the fluid enhanced or infused with mineral properties of the solid objects or stones may be gently applied to a user's skin which may avoid irritation which may otherwise be caused by application pressurized liquids or other topical formulations. Of course it is contemplated that other types of pumps and/or applicators known to those skilled in the art may be used to dispense the topical formulation from within the dispenser, such as a pump-action pump. It is also contemplated that the dispenser may dispense the topical formulation without a pump such as through a bottle-type dispenser with a snap-top cap or by, for example, pouring the formulation onto an absorbent material, such as a cotton ball or a wash cloth, which may then be topically applied to a user's skin.

In one embodiment, the opening defined by the top wall of the outer chamber may comprise threaded grooves which may allow the means for dispensing to be removably secured to the walls of the outer chambers. Of course one skilled in the art will recognize other methods of removably securing the means for dispensing are available without departing from the invention.

Thus, it is an object of the present invention to provide a dispenser configured to dispense a fluid enhanced or infused with any of a variety of beneficial and/or desirable ingredients.

It is another object of the present invention to provide a dispenser with a permeable inner chamber contained within an impermeable outer chamber to retain solid objects away from a means for dispensing the formulation.

It is yet another object of the present invention to provide a dispenser that allows a user to topically enjoy the benefits of an enhanced, aqueous formulation while avoiding having to personally mix chemicals together or carry around cumbersome devices.

One or more of the above-disclosed embodiments, in addition to certain alternatives, are provided in further detail below with reference to the attached figures. The disclosed subject matter is not, however, limited to any particular embodiment disclosed.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in any forthcoming claims; and (2) are or are potentially equivalents of express elements and/or limitations in the claims under the doctrine of equivalents.

The disclosed embodiments may be better understood by referring to the figures in the attached drawings, as provided below. The attached figures are provided as non-limiting examples for providing an enabling description of the method and system claimed. Attention is called to the fact, however, that the appended drawings illustrate only typical embodiments of this invention and are therefore not to be considered as limiting of its scope. One skilled in the art will understand that the invention may be practiced without some of the details included in order to provide a thorough enabling description of such embodiments. Well-known structures and functions have not been shown or described in detail to avoid unnecessarily obscuring the description of the embodiments.

DETAILED DESCRIPTION

Having summarized various aspects of the present disclosure, reference will now be made in detail to that which is illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims.

Figure 1:
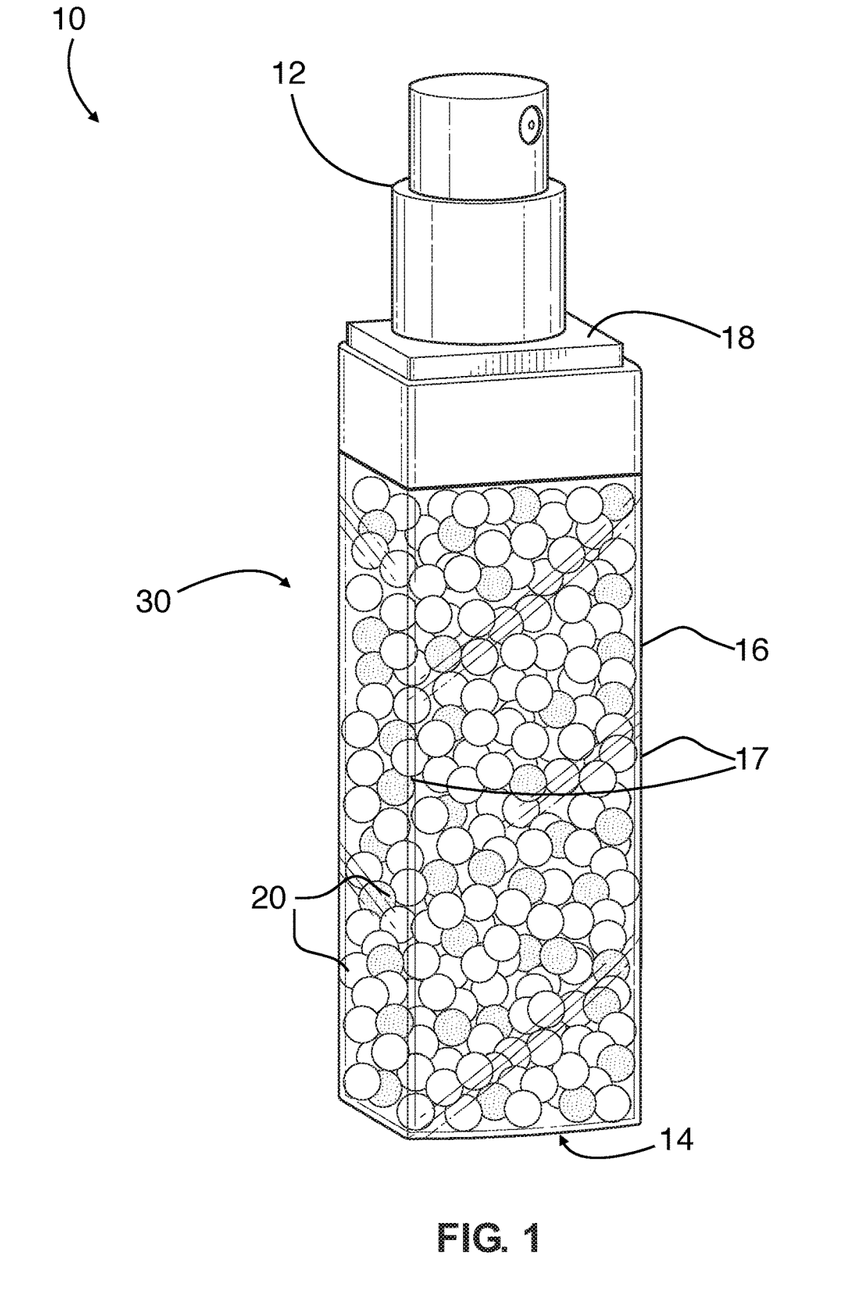
FIG. 1 shows a perspective view of the dispenser containing a plurality of solid objects in accordance with one embodiment of the invention.

With reference to FIG. 1 one embodiment of the multi-chambered dispenser 10 may comprise, in part, an impermeable outer chamber 30 configured to contain a topically applicable formulation as a fluid, such as for example, gel, foam, or liquid. Additionally, the impermeable outer chamber 30 may contain one or more solid objects, depicted for example only as a plurality of mineral stones 20, capable of infusing or otherwise enhancing the topical formulation with desirable properties. It should be noted that the solid objects may comprise any material desired to impart beneficial characteristics ingredients on fluid in communication with such objects. For example, it is known that a variety of herbs and other vegetable matter may be available to enhance fluid with vitamins and minerals known to be beneficial when topically applied to human skin. Mineral stones, however, may be preferred for their particularly long shelf-life and durability. Indeed, desirable minerals and other characteristics of the mineral stones 20 may be absorbed and/or worn away to be mixed with fluid communicating with the fluid over time, which may, among other things, prevent the formulation from becoming over-saturated.

The multi-chambered dispenser 10 may also comprise a means for dispensing 12 the fluid contained within the dispenser 10. For the sake of brevity, water, whether filtered or not, will be discussed as the fluid contained in the multi-chambered dispenser 10, however, one skilled in the art will recognize that many others are available for use with the invention. It should also be noted that although a plurality of solid objects 20 are illustrated in the figures, it will be understood that the number of solid objects 20 provided to enhance the topical formulation may be as few as one and as many any desired. Thus, for the sake of brevity, solid objects will be discussed in the plural.

In one embodiment, the impermeable outer chamber 30 may comprise a bottom wall 14, a top wall 18, and a side wall 16 spacing apart the top wall 18 and bottom wall 14, which together define an inside and an outside. It is contemplated that the bottom wall 14, top wall 18, and side wall 16 may comprise any or a combination of durable and impermeable materials such as, for example only and not limitation, plastic such as acrylic plastic and acetal resin, glass, and various metals such as aluminum. One skilled in the art, however, will recognize that other durable and impermeable materials are contemplated as well.

The side wall 16 may comprise a plurality of edges 17 so that the impermeable outer chamber 30 may be formed to define a rectangular prism, such as that shown in the figures. However, it is also contemplated that the side wall 16 may be smooth and/or edgeless so that the impermeable outer chamber 30 may define a cylinder or any other smooth shapes. It is further contemplated that the at least one side wall 16 may comprise edges and/or curves, including combinations of the same, so that the impermeable outer chamber 30 may define other polyhedral shapes. It should be noted that the foregoing are offered for the sake of example only, and the multi-chambered dispenser 10 should not be limited by any shape chosen to define the impermeable outer chamber 30. Similarly, any color comprising the bottom wall 14, top wall 18, and side wall 16 should not be seen to limit the invention. For instance, in one embodiment, the walls comprising the impermeable outer chamber 30 may be at least partially transparent. This may permit a user a view of any contents in the multi-chambered dispenser 10 including, for example, any fluid and solid objects 20 visible through the side wall 16 in FIG. 1, and even mechanical features. However, it is also contemplated that the bottom wall 14, top wall 18, and side wall 16 may be partially or wholly opaque. This may be, though is not necessarily, aesthetically desirable. As such, the particular appearance of portions of the multi-chambered dispenser 10 should not be seen to limit the invention.

Figure 2:
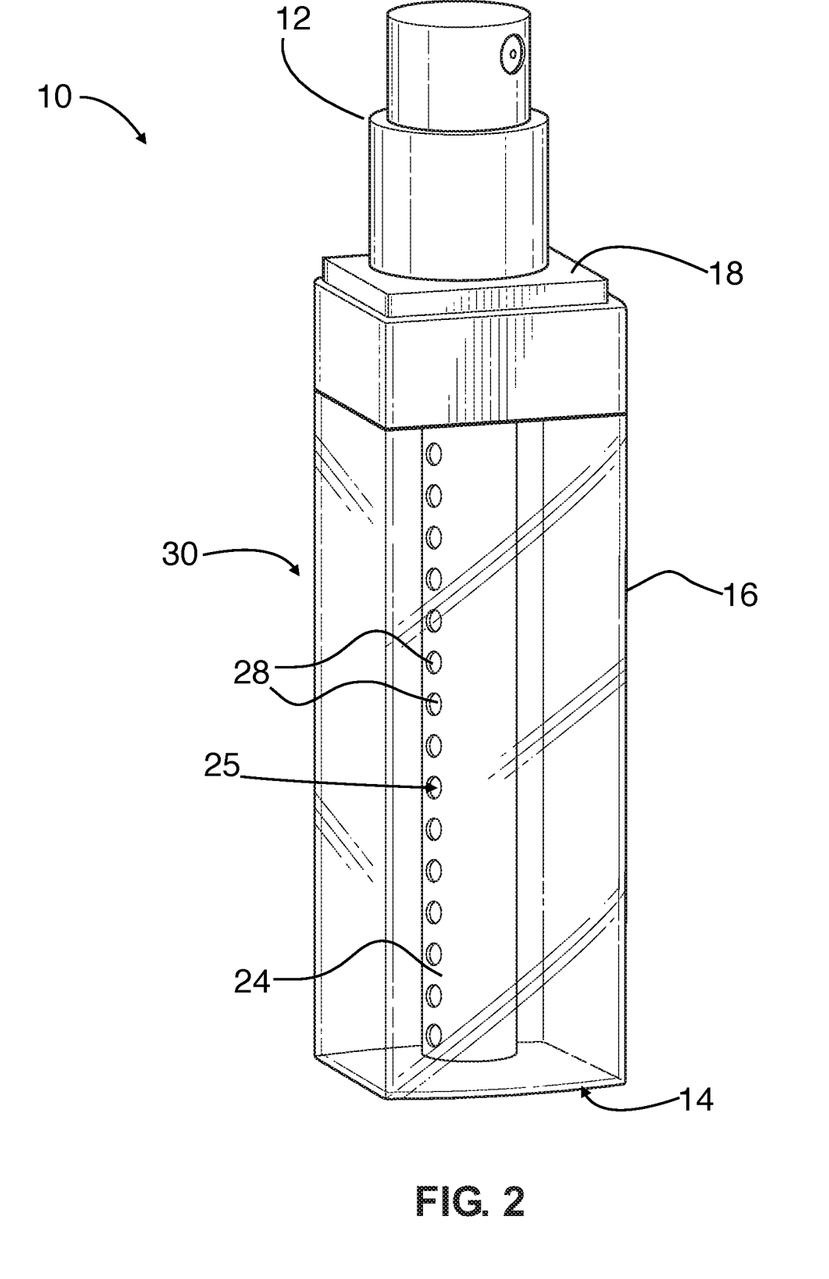
FIG. 2 shows a perspective view of the dispenser having the plurality of solid objects of FIG. 1 removed to permit view of an interior of the dispenser in accordance with one embodiment of the invention.

With reference to FIG. 2, in which the mineral stones 20 in FIG. 1 have been removed to show interior features of the multi-chambered dispenser 10, a permeable inner wall 24 may be fixed within the impermeable outer chamber 30 to define an at least one permeable inner chamber 25. A single permeable inner chamber 25 is illustrated in FIG. 2 for visual clarity, though additional permeable inner chambers, which may permit separation of mineral stones and other solid objects, for example, are contemplated by the invention.

The permeable inner wall 24 may be smooth and/or edgeless define a cylinder, such as that shown in the figures, or other smooth shape. Of course, it is contemplated that the permeable inner wall 24 may comprise edges and/or curves, including combinations of the same, so that the permeable inner wall 24 may define a polyhedral prism and other shapes. It should be noted that the foregoing are offered for the sake of example only, and the permeable inner wall 24 should not be limited by any shape chosen to define the permeable inner chamber 25.

The permeable inner wall 24 may define at least one opening 28 configured to enable fluid communication from the outside of the of the permeable inner chamber 25 to the inside of the permeable inner chamber 25, and finally out of the dispenser 10 through the means for dispensing 12. Furthermore, the at least one opening 28 may be of a size such that the mineral stones 20 in FIG. 1, or any other solid object retained outside of the permeable inner chamber 25, may be prevented from entering the inner permeable chamber 24 to avoid interference with operation of the means for dispensing 12 fluid.

Figure 3:
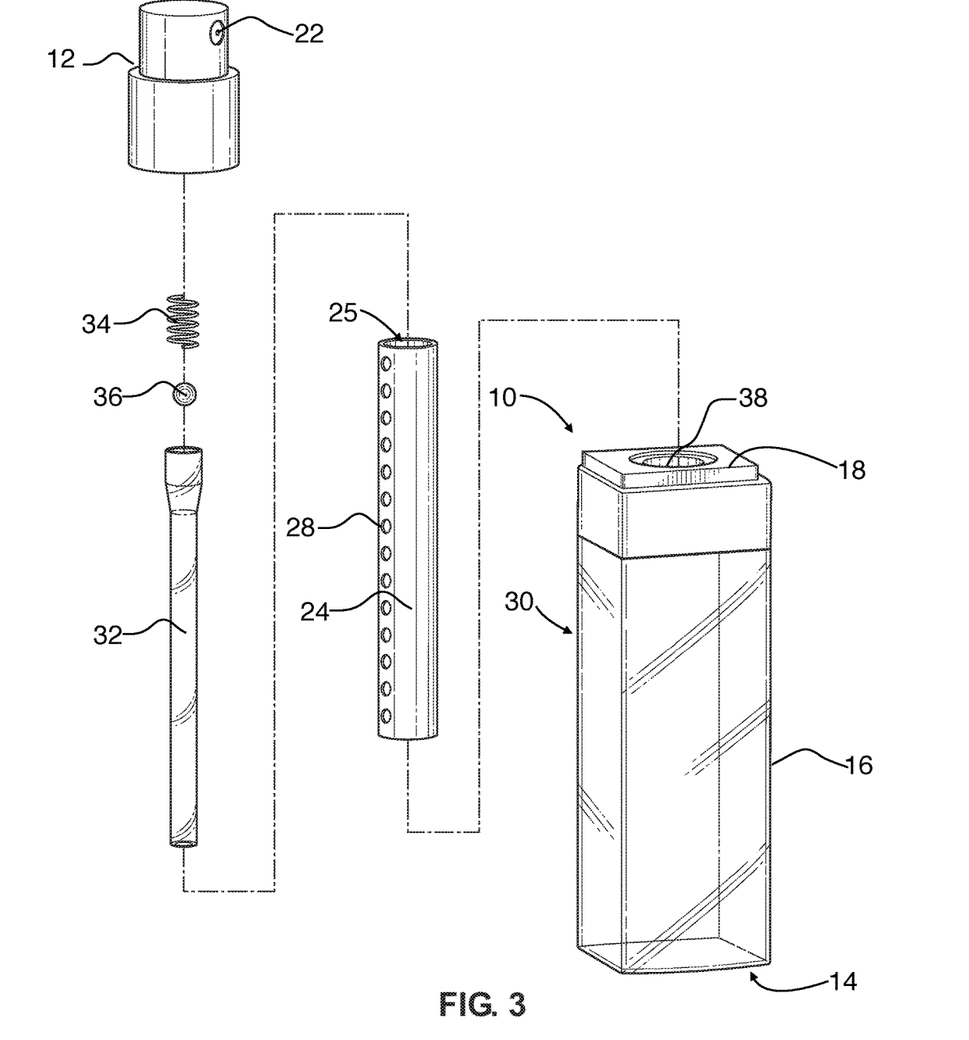
FIG. 3 shows an exploded view of the dispenser in accordance with one embodiment of the invention.

With reference to the exploded view of the multi-chambered dispenser 10 in FIG. 3, the top wall 18 may define an opening 38 which can securely receive the means for dispensing 12 fluid. The means for dispensing 12 may be releasably securable to the top wall 18 by way of any means for releaseable securement known in the art. It is contemplated that the means for releaseable securement may comprise mateably threaded grooves that may allow a user to simply screw the means for dispensing 12 onto and off of the multi-chambered dispenser 10. Of course, other means of attachment such as, for example only and not limitation, a snap-fit mechanism and snap buttons, are considered by the invention.

In one embodiment, the means for dispensing 12 fluid may be a mist sprayer pump having a tube 32 extensible through the permeable inner chamber 25. Various elements known to those skilled in the art may be provided, such as a spring 34 and plugging mechanism 36 to effect positive displacement of any topical formulation so that such formulation may be ultimately dispensed from the multi-chambered dispenser 10 through mouth 22. However, other means for dispensing 12 fluid are contemplated by the invention. For example, the means for dispensing 12 fluid may comprise a pump-action pump and a snap-top cap. Indeed, in some embodiments, it is contemplated that fluid enhanced or infused with desirable characteristics of mineral stones or other solid objects may be poured directly from the uncovered opening 38 defined by the top wall 18 in any desirable amount onto an absorbent material, such as but not limited to a cotton ball or wash cloth.

When the opening 38 is exposed, a fluid may be directly poured into the multi-chambered dispenser 10 through the opening 38 defined by the top wall 18 to permit communication, and ultimately infusion, with the mineral stones or other solid objects retained outside of the permeable inner wall 24.

In an embodiment, holes 28 or other voids characterizing the permeability of the permeable inner wall 24 enable fluid such as water contained within the multi-chambered dispenser 10 to communicate with the mineral stones 20 of FIG. 1 contained between the permeable inner wall 24 and the impermeable outer walls 14, 16, 18. The at least one opening 28 may be sized so as to prevent the mineral stones 20, or other one or more solid objects, from entering the permeable inner chamber 25 and disrupting the fluid communication of any topical formulation through the chambers of the multi-chambered dispenser 10.

Figure 4:
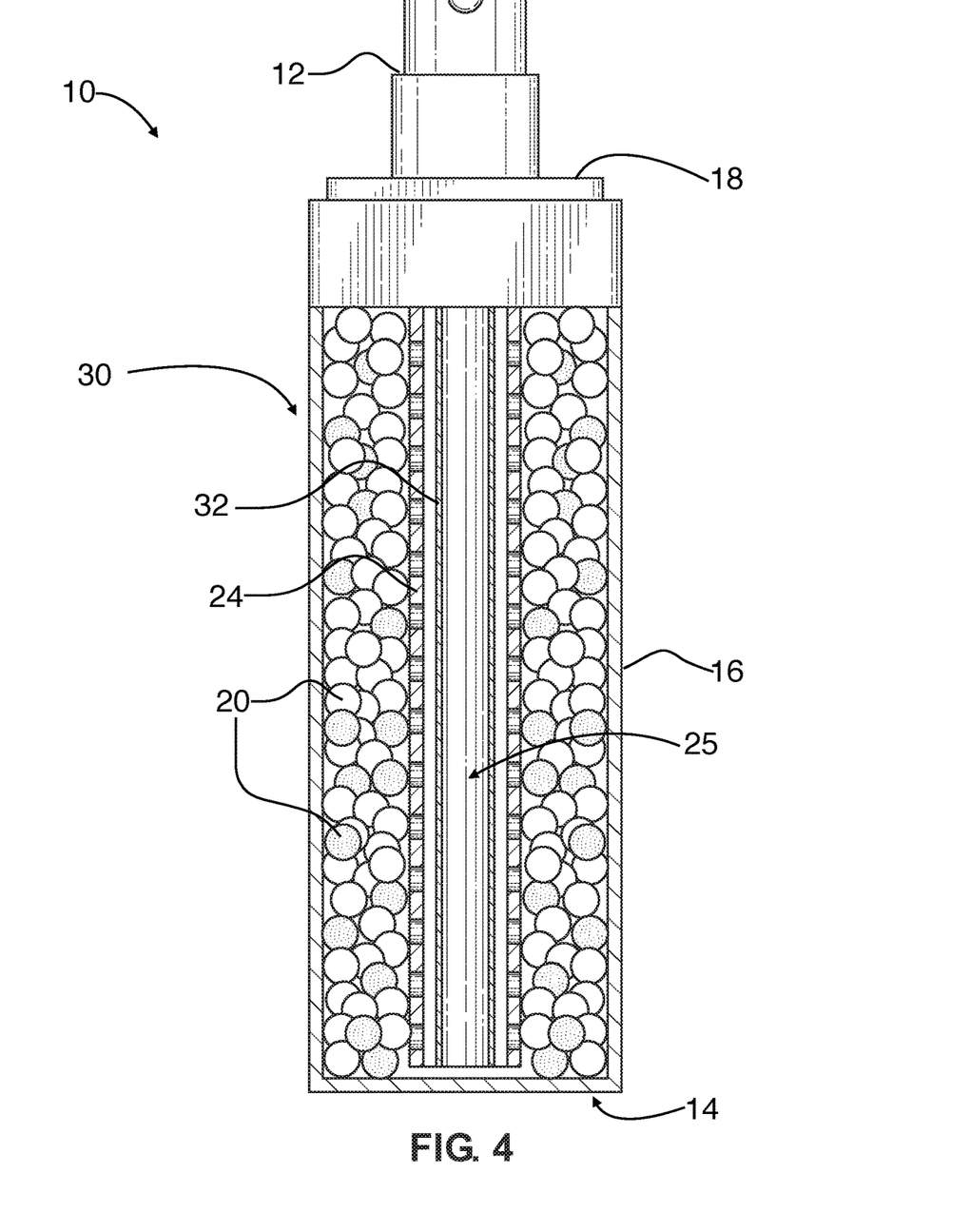
FIG. 4 illustrates a cross-sectional view of the dispenser in accordance with one embodiment of the invention.

With reference to FIG. 4, the multi-chambered dispenser 10 may be filled with the topical formulation and the solid objects 20. The solid objects, shown as mineral stones 20, may be composed of any substance, compound, mineral, or the equivalent thereof having qualities and characteristics that may desirably enhance or alter the characteristics of the contained fluid. For example, it is contemplated that the mineral stones 20 may be comprise substances known or thought to increase the alkalinity of the water contained within the multi-chambered dispenser 10. In order to increase the topical formulation's alkalinity, the mineral stones 20 may comprise, for example, tourmaline, sepiolite, negative ion powder, ascorbic acid, germanium, magnesium, calcium, or ceramic minerals. The use of such 20 may cause the pH level of the water to increase and become more alkaline. The mineral stones 20 may be maintained between the permeable inner wall 24 that defines the permeable inner chamber 25 and the outer walls 14, 16, 18 that define the impermeable outer chamber 30.

The at least one opening 28 of FIG. 2, defined by the permeable inner wall 24, may be of any shape and size able to prevent the mineral stones 20 or other one or more solid objects from entering the inner permeable chamber 25 and interfering with the operation of the means for dispensing 12 fluid. This configuration may prevent the mineral stones 20 from disrupting the flow of the topical formulation through the multi-chambered dispenser 10. However, other means of creating a permeable chamber are considered by the invention. For example, it is contemplated that any porous material durable enough to preclude the mineral stones 20 or other one or more solid objects from entering the permeable inner chamber 25 while still allowing the topical formulation to communicate between the impermeable outer chamber 30 and the permeable inner chamber 25 may be used to create the permeable inner wall 24. Such porous and durable materials include, but are not limited to, durable mesh, PVC, and metal, among others.

Furthermore, it is contemplated that the permeable inner wall 24 may extend from the impermeable bottom wall 14 to the means for dispensing 12 to define a superposed extension of the at least one opening 38 defined by the top wall 18 into the impermeable outer chamber 30. With this configuration, the mineral stones 20 may be prevented from breaching the permeable inner chamber 25 and negatively affecting the flow of the topical formulation through the multi-chambered dispenser 10.

Thus, any fluid contained in the multi-chambered dispenser 10 may become enhanced by absorbing the minerals and other elements comprising the mineral stones 20 in by dissolving or washing off portions of the mineral stones 20, or other solid objects in FIG. 1. The infused or enhanced fluid may then be transported through the tube 32 and dispersed from the mouth 22 of the means for dispensing 12 fluid so that the fluid may be applied as a topical formulation by the user.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

CONCLUSIONS, RAMIFICATIONS, AND SCOPE

While certain embodiments of the invention have been illustrated and described, various modifications are contemplated and can be made without departing from the spirit and scope of the invention. For example, the appearance and shape of the dispenser, and particularly walls of the outer chamber, may take various forms as may be functionally or aesthetically desired. Additionally, the plurality of mineral stones may be arranged in an aesthetically desirable manner viewable through the walls of the outer chamber without departing from the invention. Accordingly, it is intended that the invention not be limited, except as by the appended claim(s).

The teachings disclosed herein may be applied to other systems, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the multi-chambered dispenser for the topical application of infused fluid with which that terminology is associated. In general, the terms used in the following claims should not be constructed to limit the multi-chambered dispenser for the topical application of infused fluid to the specific embodiments disclosed in the specification unless the above description section explicitly define such terms. Accordingly, the actual scope encompasses not only the disclosed embodiments, but also all equivalent ways of practicing or implementing the disclosed apparatus. The above description of embodiments of the multi-chambered dispenser for the topical application of infused fluid is not intended to be exhaustive or limited to the precise form disclosed above or to a particular field of usage.

While specific embodiments of, and examples for the apparatus are described above for illustrative purposes, various equivalent modifications are possible for which those skilled in the relevant art will recognize.

While certain aspects of the method and system disclosed are presented below in particular claim forms, various aspects of the apparatus are contemplated in any number of claim forms. Thus, the inventor reserves the right to add additional claims after filing the application to pursue such additional claim forms for other aspects of the multi-chambered dispenser for the topical application of infused fluid.

What is claimed is:

1. A multi-chambered topical dispenser for topical application of a mineral enhanced solution, comprising:
   an outer chamber having an inside and an outside, wherein the outer chamber is impermeable, and wherein the outer chamber is defined by a bottom wall spaced apart from a top wall by a side wall, the side wall extending between the top and bottom walls, the top wall further defining an opening into the outer chamber;
   at least one permeable inner chamber having an inside and an outside, the inner permeable chamber defined by a permeable inner wall having at least one wall opening therethrough to enable at least one fluid contained by the dispenser to communicate between the permeable inner chamber and the outer chamber;
   at least one solid mineral stone contained in the outer chamber, the at least one solid mineral stone having a size that is larger than the at least one wall opening so as to be unable to fully enter the permeable inner chamber, wherein the at least one solid mineral stone is operative to infuse the at least one fluid with at least one property of the at least one solid mineral stone;
   wherein the permeable inner wall is contained within the outer chamber and wherein the permeable inner wall is configured to extend from the bottom wall to the opening into the outer chamber defined by the top wall; and
   a dispenser tube for dispensing the at least one fluid, the dispenser tube being positioned within the permeable inner chamber such that the dispenser tube passes into the permeable inner chamber and is circumferentially surrounded by the permeable inner chamber.

2. The multi-chambered dispenser of claim 1, further comprising a means for dispensing the at least one fluid, wherein the means for dispensing the at least one fluid is removably securable to a portion of the top wall defining the outer chamber.

3. The multi-chambered dispenser of claim 2, wherein the means for dispensing the at least one fluid is a mist sprayer pump.

4. The multi-chambered dispenser of claim 1, wherein the at least one permeable inner wall defines a superposed extension of the opening into the impermeable outer chamber.

5. The multi-chambered dispenser of claim 1, wherein the at least one mineral stone is operative to release at least one of tourmaline, sepiolite, negative ion powder, ascorbic acid, germanium, magnesium, calcium, and ceramic minerals.

6. The multi-chambered dispenser of claim 1, wherein the means for dispensing the at least one fluid is operative to dispense the at least one fluid contained in the permeable inner chamber.

7. The multi-chambered dispenser of claim 1, wherein the at least one mineral stone is comprised of at least one of tourmaline, sepiolite, solidified negative ion powder, solidified ascorbic acid, germanium, magnesium, calcium, ceramic minerals, and muyu jade stone.

8. The multi-chambered dispenser of claim 1, wherein each of the at least one permeable inner chamber and dispenser tube have a length, such that the dispenser tube passes into the at least one permeable inner chamber for substantially the entire length of the at least one permeable inner chamber.

9. The multi-chambered dispenser of claim 1, wherein a space exists between the outer chamber and at least one permeable inner chamber, with the at least one solid object including a plurality of solid objects that fill the space between the outer chamber and at least one permeable inner chamber.

10. A multi-chambered topical dispenser for topical application of a mineral enhanced solution, comprising:

a watertight outer chamber, comprising
- a) at least one outer chamber side wall;
- b) at least one outer chamber bottom wall; and
- c) at least one outer chamber top wall, wherein the at least one outer chamber top wall defines at least one opening;

at least one inner chamber positioned within the watertight outer chamber, comprising:
- a) at least one inner chamber wall having a top inner chamber wall side and a bottom inner chamber wall side, wherein the top inner chamber wall side is connected to the at least one outer chamber top wall, and wherein the bottom inner chamber wall side is in contact with the outer chamber bottom wall; and
- b) a plurality of holes defined along the at least one inner chamber wall, wherein the plurality of holes are configured to transverse the at least one inner chamber wall;

at least one fluid configured to traverse between the outer chamber and the inner chamber;

a means for dispensing the at least one fluid having at least one intake tube, wherein the means for dispensing the at least one fluid is configured to removably secure to the top wall, and A wherein the at least one intake tube has a length with a vertical axis that is with a circumference of the at least one inner chamber; and at least one mineral stone contained in the outer chamber, wherein the at least one mineral stone is operative to release a mineral substance into the at least one fluid, and wherein the at least one mineral stone having a size such that it is unable to pass through the plurality of holes.

11. The dispenser of claim 10, wherein:
a) the at least one outer chamber side wall is one arcuate outer chamber side wall having an arcuate outer chamber side wall top side and an arcuate outer chamber side wall bottom side;
b) the at least one bottom wall has one arcuate bottom wall side configured to create a watertight seal with the arcuate outer chamber side wall bottom side; and
c) the at least one top wall has one arcuate top wall side configured to create a watertight seal with the arcuate outer chamber side wall top side.

12. The dispenser of claim 10, wherein:
d) the at least one outer chamber side wall is three rectangular outer chamber side walls, each outer chamber side wall having two outer chamber short sides and two outer chamber long sides, wherein each outer chamber long side is configured to create a watertight seal with one outer chamber long side;
e) the at least one bottom wall has three bottom wall sides, wherein each bottom wall side is configured to create a watertight seal with one outer chamber short side; and
f) the at least one top wall has three top wall sides, wherein each top wall side is configured to create a watertight seal with one outer chamber short side.

13. The dispenser of claim 10, wherein:
a) the at least one outer chamber side wall is four rectangular outer chamber side walls, each outer chamber side wall having two outer chamber short sides and two outer chamber long sides, wherein each outer chamber long side is configured to create a watertight seal with one outer chamber long side;
b) the at least one bottom wall has four bottom wall sides, wherein each bottom wall side is configured to create a watertight seal with one outer chamber short side; and
c) the at least one top wall has four top wall sides, wherein each top wall side is configured to create a watertight seal with one outer chamber short side.

14. The dispenser of claim 10, further comprising at least two distinct layers of mineral stones, such that the mineral stones in a first layer are comprised of a different type of mineral stones than the mineral stones in a second layer, with the mineral stones being positioned within the outer chamber in the two distinct layers such that a distinct delineation exists between the at least two distinct layers.

15. The dispenser of claim 14, wherein:
a) one of the at least two layers of mineral stones is a layer of mineral stones operative to release magnesium; and
b) one of the at least two layers of mineral stones is a layer of mineral stones operative to release tourmaline.

16. The dispenser of claim 14, wherein:
a) one of the at least two layers of mineral stones is a layer of mineral stones comprised of magnesium; and
b) one of the at least two layers of mineral stones is a layer of mineral stones comprised of tourmaline.

17. The dispenser of claim 10, further comprising at least one transparent element disposed on at least one outer chamber side wall, wherein the at least one transparent element is configured to transverse the at least one side wall, and wherein the at least one transparent element is configured to display at least one mineral stone.

18. The dispenser of claim 10, wherein the means for dispensing the at least one fluid is a mist sprayer pump.

19. The dispenser of claim 10, wherein the means for dispensing the at least one fluid is a bottle-type dispenser with a snap-top cap.

20. A method for topical application of a mineral enhanced solution, comprising steps of:
introducing a fluid into a multi-chambered topical spray dispenser, the multi-chambered topical spray dispenser having an impermeable outer chamber filled with mineral stones and permeable inner chamber free of mineral stones, such that upon introducing the fluid into the multi-chambered topical spray dispenser, the fluid passes through the permeable inner chamber and into the impermeable outer chamber, where the fluid interacts with the mineral stones and becomes a mineral enhanced solution and flows back into the permeable inner chamber; and pumping a spray actuator to dispense the mineral enhanced solution onto a user's skin surface, the spray actuator having a dispenser tube being positioned within the permeable inner chamber such that the dispenser tube passes into the permeable inner chamber and is circumferentially surrounded by the permeable inner chamber, wherein pumping the spray actuator causes the mineral enhanced solution to pass through the dispenser tube and out of the multi-chambered topical spray dispenser onto the user's skin surface for topical application of the mineral enhanced solution.

\* \* \* \* \*